(12) United States Patent
Bian et al.

(10) Patent No.: US 9,408,828 B2
(45) Date of Patent: Aug. 9, 2016

(54) (+)-3'-ANGELOYLOXY-4'-KETO-3',4'-DIHYDROSESELIN FOR TREATING INFLAMMATION

(71) Applicants: Hong Kong Baptist University, Hong Kong (HK); Changshu Research Institute of Hong Kong Baptist University, Jiangsu (CN)

(72) Inventors: Zhaoxiang Bian, Hong Kong (HK); Huaixue Mu, Hong Kong (HK); Chengyuan Lin, Hong Kong (HK); Quanbin Han, Hong Kong (HK); Aiping Lu, Hong Kong (HK); Linfang Huang, Hong Kong (HK); Shilin Chen, Hong Kong (HK); Dajian Yang, Hong Kong (HK); Hongxi Xu, Hong Kong (HK); Sun Chi Albert Chan, Hong Kong (HK)

(*) Notice: Subject to any disclaimer, the term of this patent is extended or adjusted under 35 U.S.C. 154(b) by 0 days.

(21) Appl. No.: 14/742,727

(22) Filed: Jun. 18, 2015

(65) Prior Publication Data
US 2015/0366841 A1 Dec. 24, 2015

Related U.S. Application Data

(60) Provisional application No. 62/013,566, filed on Jun. 18, 2014.

(51) Int. Cl.
*A61K 31/37* (2006.01)
*A61K 31/366* (2006.01)
*A61K 9/00* (2006.01)

(52) U.S. Cl.
CPC .............. *A61K 31/366* (2013.01); *A61K 9/0053* (2013.01); *A61K 31/37* (2013.01)

(58) Field of Classification Search
CPC ...................................................... A61K 31/37
See application file for complete search history.

(56) References Cited

U.S. PATENT DOCUMENTS

2005/0222245 A1* 10/2005 Yoon .................... C07D 493/04
514/454

OTHER PUBLICATIONS

Scott, Jennifer. Everyday Health.com: Autoimmune Digestive disorders, 2009, pp. 1-4.*
Yu et al. Inflammation, 2012, vol. 35, No. 3, pp. 967-977.*
Jiang et al., "Beneficial Effect of Bupleurum Polysaccharides on Autoimmune-Prone MRL-lpr Mice", Clin Dev Immunol. 2012, 2002, 842928.
Moga, M. M., "Alternative treatment of gallbladder disease". Med. Hypotheses 2003, 60, 143.
Ashour and Wink, "Genus Bupleurum: a review of its phytochemistry, pharmacology and modes of action", Journal of Pharmacy and Pharmacology 2011; 63: 305-321.
Chen et al., "Saikosaponin a and Saikosaponin d Inhibit Proliferation and Migratory Activity of Rat HSC-T6 Cells", J Med Food 16 (9) 2013, 793-800.
Lu et al., "Saikosaponin a and its epimer saikosaponin d exhibit anti-inflammatory activity by suppressing activation of NF-κB signaling pathway", International Immunopharmacology 14 (2012) 121-126.
Li et al., "Neuroprotective effects of Total Saikosaponins of Bupleurum yinchowense on corticosterone-induced apoptosis in PC12 cells", Journal of Ethnopharmacology 148 (2013) 794-803.
Li et al., "High Performance Liquid Chromatographic Assay of Saikosaponins from Radix Bupleuri in China", Biol. Pharm. Bull. 28(9) 1736-1742 (2005).
Li et la., "Essential Oil Analyses of the Root Oils of 10 Bupleurum Species From China", J. Essent. Oil Res., 19, 234-238 (May/Jun. 2007).
Li et al, "GC Fingerprint analysis for quality control of volatile oil in Radix Bupleuri", Chinese Traditional and Herbal Drugs, 37, 8, 1165-1167 (Aug. 2006).
Zhang et al., "Chemical constituents from roots of *Peucedanum praeruptorum* (V)", China Journal of Chinese Materia Medics, vol. 37, Issue 23, 3573-3576 (Dec. 2012).
Wang et al., "(+)-(3'R)-Angeloyloxy-4'-oxo-3',4'-dihydroseselin (Pd-lb)", Acta Cryst. (2006). E62, o2505-o2507.
Liu et al., "Preparative isolation and purification of coumarins from Peucedanum praeruptorum Dunn by high-speed counter-current chromatography", Journal of Chromatography A, 1057 (2004) 89-94.
Constantinescu et al., "Exocrine cell-derived microparticles in response to lipopolysaccharide promote endocrine dysfunction in cystic fibrosis", Journal of Cystic Fibrosis, 13 (2014) 219-226.
Xiao et al., "Inhibitory Effect of the Gallotannin Corilagin on Dextran Sulfate Sodium-Induced Murine Ulcerative Colitis", J. Nat. Prod. 2013, 76, 2120-2125.
Yan et al., "Activating glucocorticoid receptor-ERK signaling pathway contributes to ginsenoside Rg1 protection against β-amyloid peptide-induced human endothelial cells apoptosis", Journal of Ethnopharmacology 147 (2013) 456-466.
DeVon et al., "The Association of Pain With Protein Inflammatory Biomarkers", Nursing Research Jan./Feb. 2014 vol. 63, No. 1, 51-62.
Lim et al., "Inhibition of Proinflammatory Cytokine Generation in Lung Inflammation by the Leaves of Perilla frutescens and Its Constituents", Biomol Ther 22(1), 62-67 (2014).
Yang et al., "Inhibitory Effect of Litchi (*Litchi chinensis* Sonn.) Flower on Lipopolysaccharide-Induced Expression of Proinflammatory Mediators in RAW264.7 Cells through NF-κb, ERK, and JAK2/STAT3 Inactivation", J. Agric. Food Chem. 2014, 62, 3458-3465.
Fugen Aktan, "iNOS-mediated nitric oxide production and its regulation", Life Sciences 75 (2004) 639-653.

(Continued)

*Primary Examiner* — Samira Jean-Louis
(74) *Attorney, Agent, or Firm* — Ella Cheong Hong Kong; Sam T. Yip

(57) ABSTRACT

The present invention provides a compound, namely (+)-3'-Angeloyloxy-4'-keto-3',4'-dihydroseselin (Pd-Ib) derived from *Bupleurum malconense* as the potential anti-inflammation drug. The present invention also relates to methods of preparing the compounds and using the same for treating inflammation.

6 Claims, 14 Drawing Sheets

(56) References Cited

OTHER PUBLICATIONS

Zhou et al., "Biflavonoids from Caper (*Capparis spinosa* L.) Fruits and Their Effects in Inhibiting NF-kappa B Activation", J. Agric. Food Chem. 2011, 59, 3060-3065.

Zhang et al., "Mesenchymal Stem Cells Secrete Immunologically Active Exosomes", Stem Cells Dev. Jun. 1, 2014;23 (11):1233-44.

Barnes and Karin, "Nuclear Factor-Kb—A Pivotal Transcription Factor in Chronic Inflammatory Disease", N Engl J Med. Apr. 10, 1997;336(15):1066-71.

Lundberg et al., "Greatly Increased Luminal Nitric Oxide in Ulcerative Colitis", Lancet 1994; 344: 1673-74.

Müzes et al., "Changes of the cytokine profile in inflammatory bowel diseases", World J Gastroenterol Nov. 7, 2012; 18(41): 5848-5861.

Candiracci et la., "Anti-inflammatory Activity of a Honey Flavonoid Extract on Lipopolysaccharide-Activated N13 Microglial Cells", J. Agric. Food Chem. 2012, 60, 12304-12311.

Pile et al., "Interventional Effects of Plumbagin on Experimental Ulcerative Colitis in Mice", J. Nat. Prod. 2013, 76, 1001-1006.

Giner et al., "Oleuropein Protects against Dextran Sodium Sulfate-Induced Chronic Colitis in Mice", J. Nat. Prod. 2013, 76, 1113-1120.

Andujar et al., "Inhibition of Ulcerative Colitis in Mice after Oral Administration of a Polyphenol-Enriched Cocoa Extract Is Mediated by the Inhibition of STAT1 and STAT3 Phosphorylation in Colon Cells", J. Agric. Food Chem. 2011, 59, 6474-6483.

Wadie et al., "STW 5 is effective in dextran sulfate sodium-induced colitis in rats", Int J Colorectal Dis (2012) 27:1445-1453.

Reagan-Shaw et al., "Dose translation from animal to human studies revisited", The FASEB Journal, vol. 22 Mar. 2007, 659-661.

Kang et al., "Four New Neuroprotective Dihydropyranocoumarins from Angelica gigas", J. Nat. Prod. 2005, 68, 56-59.

Rosselli et al., "The Cytotoxic Properties of Natural Coumarins Isolated from Roots of Ferulugoc ampestris (Apiaceaea) and of Synthetic Ester Derivatives of Aegelinol", Nat Prod Commun. Dec. 2009;4(12):1701-6.

Nakamura et al., "The structure-activity relationship between oxycoumarin derivatives showing inhibitory effects on NOS in mouse macrophage RAW264.7 cells", J Nat Med (2009) 63:15-20.

\* cited by examiner

Figure 8 (Con't)
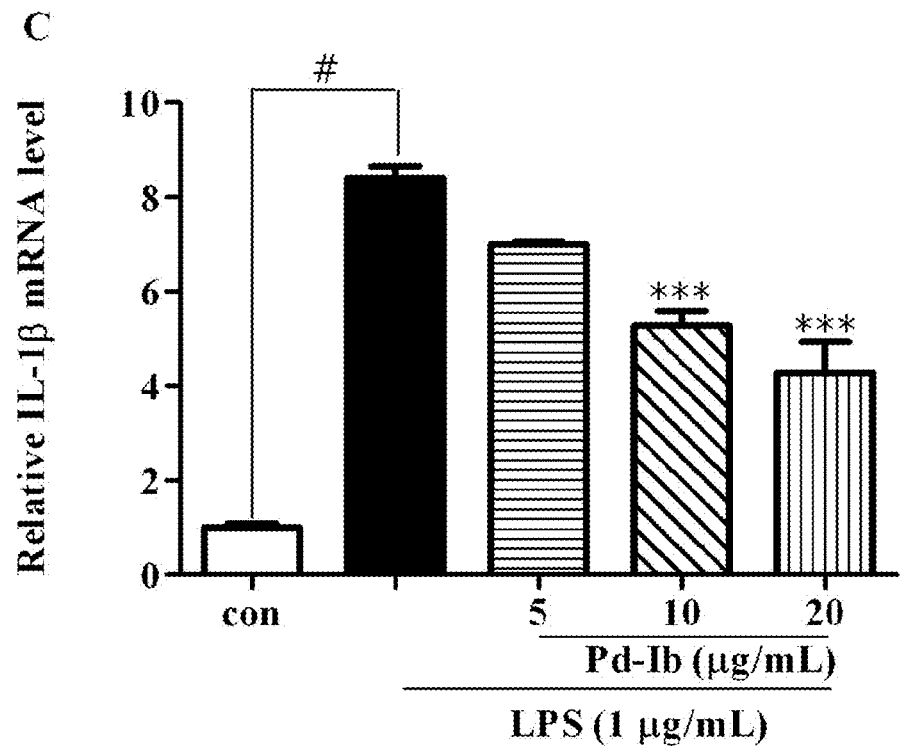
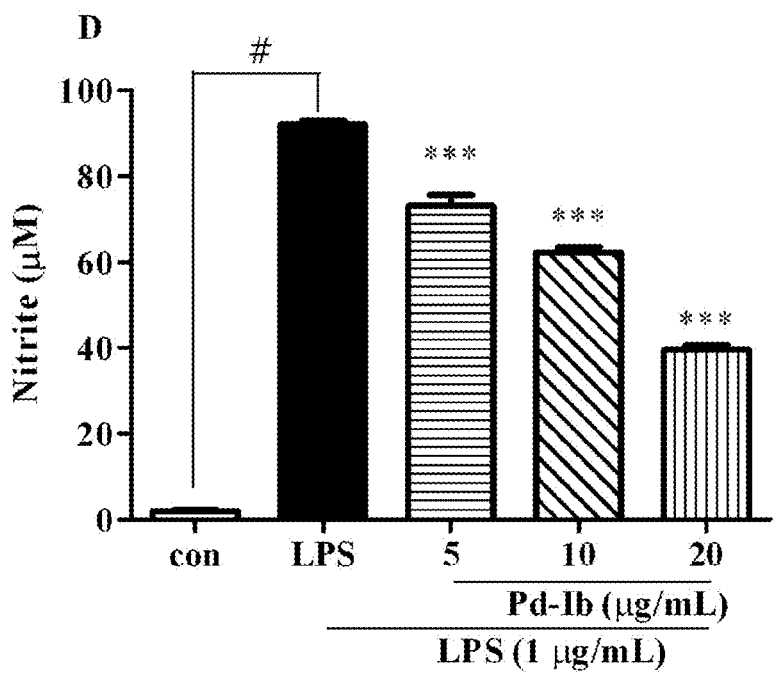

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
caccttggag ttcacccagt                                             20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
accactcgta cttgggatgc                                             20

<210> SEQ ID NO 3
<211> LENGTH: 20
<212> TYPE: DNA
<213> ORGANISM: Artificial Sequence
<220> FEATURE:
<223> OTHER INFORMATION: Primer
```

```
<400> SEQUENCE: 3
ctgtgaaggg aatgggtgtt                                              20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
ggtcactgtc ccagcatctt                                              20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
gctgaaggag ttgccagaaa                                              20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
gtgcaagtga ctcagggtga                                              20

<210> SEQ ID NO 7
<211> LENGTH: 19
<212> TYPE: DNA
<213> ORGANISM: Artificial Sequence
<220> FEATURE:
<223> OTHER INFORMATION: Primer

<400> SEQUENCE: 7
ggtgaaggtc ggtggaacg                                               19

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
ctcgctcctg gaagatggtg                                              20
```

(+)-3'-ANGELOYLOXY-4'-KETO-3',4'-DIHYDROSESELIN FOR TREATING INFLAMMATION

CROSS-REFERENCE TO RELATED APPLICATIONS

The present application claims priority of U.S. Provisional Patent Application Ser. No. 62/013,556 filed Jun. 18, 2014, and which the disclosure is hereby incorporated by reference in its entirety.

FIELD OF INVENTION

The present invention is in the field of pharmaceuticals and chemical industries. In particular, the present invention relates to a compound, namely (+)-3'-Angeloyloxy-4'-keto-3,4'-dihydroseselin (Pd-Ib). The present invention also includes the methods of preparation and use thereof for treating inflammation, such as in alleviating the symptoms of dextran sulfate sodium (DSS)-induced chronic colitis and being used as an effective treatment against ulcerative colitis.

BACKGROUND OF INVENTION

Previous studies showed in Jiang, Y. W., et al., Beneficial effect of *Bupleurum polysaccharides* on autoimmune-prone MRL-lpr mice. *Clin Dev Immunol*. 2012, 2002, 842928 and Moga, M. M., et al., Alternative treatment of gallbladder disease. *Med. Hypotheses* 2003, 60, 143 that *Bupleurum* is a member of the Apiaceae family of plants and one of the most popular herbs, which is used for treatment of inflammation-related disease, such as autoimmune diseases, inflammatory bowel syndrome, cholecystitis. So far, nearly 50 *Bupleurum* species have been extensively studied for their phytochemical characteristic. Some of them have been developed into food supplements because of their low side effects, low cost and non-toxicity. Saikosaponins are commonly recognized as the main components responsible for the bioactivity of *Bupleurum* species; however, it appears no saponins have been found in *Bupleurum malconense*.

Interestingly, the petroleum ether extract of *Bupleurum malconense* exerted strong ameliorative effects on colon shortening and loss of the body weight. Because saikosponins are polar chemical and cannot exist in the petroleum ether extract, we assumed that other kinds of compounds rather than saikosponins should be responsible for the anti-inflammatory propertied in the petroleum ether extract of *Bupleurum malconense*.

Thus, the aim of present invention is to identify the major anti-inflammatory component in the petroleum ether extract of *Bupleurum malconense* using bioassay-guided fractionation. The anti-inflammatory mechanisms of this active compound are then examined in vitro, e.g., in LPS-stimulated murine macrophage RAW-Blue cells. In vivo study of the anti-inflammatory effect of the major component is also performed in a disease animal model with inflammatory diseases such as ulcerative colitis to demonstrate the efficacy of the major anti-inflammatory component and determine its therapeutically effective amount.

Citation or identification of any reference in this section or any other section of this application shall not be construed as an admission that such reference is available as prior art for the present application.

SUMMARY OF INVENTION

Accordingly, the objective of the present invention is to provide one compound, namely (+)-3'-Angeloyloxy-4'-keto-3,4'-dihydroseselin (Pd-Ib), for use as an anti-inflammation drug candidate through inhibition of NF-κB and iNOS activation.

In one aspect of the present invention, a method for treating inflammation comprising administering to a subject in needs thereof an effective amount of a compound of structure (I) is provided:

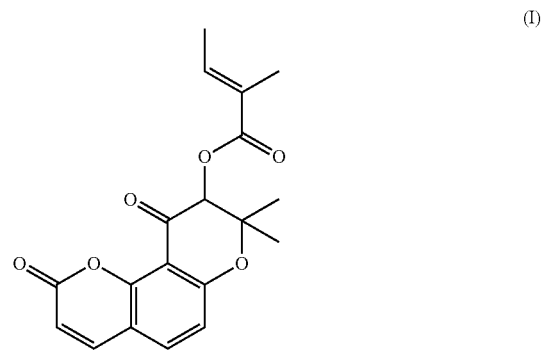 [SMILES: C/C=C(\C)C(=O)OC1C(=O)c2c(ccc3ccc(=O)oc23)OC1(C)C]

(I)

In one embodiment, the effective amount of said compound being administered according to the method of the present invention ranges from 2.43 to 9.72 mg/kg/day of the subject's body weight and said subject is human. Said effective amount of the compound of the present invention is orally administered daily to said subject for at least seven consecutive days after the onset of the inflammation or inflammatory diseases.

In another embodiment, the effective amount of said compound being administered according to the method of the present invention is about 9.72 mg/kg/day of the subject's body weight and said subject is human. Said effective amount of the compound of the present invention is orally administered daily to said subject for at least seven consecutive days after the onset of the inflammation or inflammatory diseases.

Those skilled in the art will appreciate that the present invention described herein is susceptible to variations and modifications other than those specifically described.

The present invention includes all such variation and modifications. The present invention also includes all of the steps and features referred to or indicated in the specification, individually or collectively, and any and all combinations or any two or more of the steps or features.

Throughout the present specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the present invention.

Furthermore, throughout the present specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the present invention and apply throughout. Unless otherwise defined, all other technical terms used herein have the same meaning as commonly understood to one of ordinary skill in the art to which the invention belongs.

Other aspects and advantages of the present invention will be apparent to those skilled in the art from a review of the ensuing description.

BRIEF DESCRIPTION OF DRAWINGS

The above and other objects and features of the present invention will become apparent from the following description of the invention, when taken in conjunction with the accompanying drawings, in which.

DETAILED DESCRIPTION OF INVENTION

The present invention is not to be limited in scope by any of the specific embodiments described herein. The following embodiments are presented for exemplification only.

General Experimental Procedures

Chemicals

LPS (lipopolysaccharides, L3129), MTT (3-[4,5-dimethylthiazol-2-yl]-2,5-diphenyltetrazoliumbromide) and DMSO (dimethyl sulfoxide), Griess reagent, and all chemicals used are of HPLC grade from Sigma Chemical Co. (St. Louis, Mo., USA). Primer for iNOS, IL-1β, TNF-α, Trizol, SYBR Green, DMEM (Dulbecco's modified Eagle's medium), ECL reagent, fetal bovine serum, penicillin and streptomycin are purchased from Life Technologies (Carlsbad, Calif., USA) and BCA protein assay kit is supplied by Thermo Fisher Scientific (Waltham, Mass., USA). NF-κB, IκB-α, COX-2 and iNOS rabbit antibody are purchased from Cell Signaling Technology (Beverly, Mass., USA). β-Actin mouse antibody, anti-rabbit IgG and anti-mouse IgG are purchased from Santa Cruz Biotechnology (Santa Cruz, Calif., USA). QUANTI-Blue medium and Alexa Fluor568@ anti-rabbit IgG are purchased from Invivo Gen (San Diego, Calif., USA). Fractions are monitored and combined by thin layer chromatography (TLC). Spots are made visible by heating silica gel plates that had been immersed in 5% $H_2SO_4$ in EtOH. Sulfasalazine is purchased from Sigma Corp. (Louis, USA). Dextran sulfate sodium (DSS; molecular weight: 36 to 50 kDa) is purchased from MP Biomedical (Santa Ana, Calif., USA).

Plant Material

Figure 1:
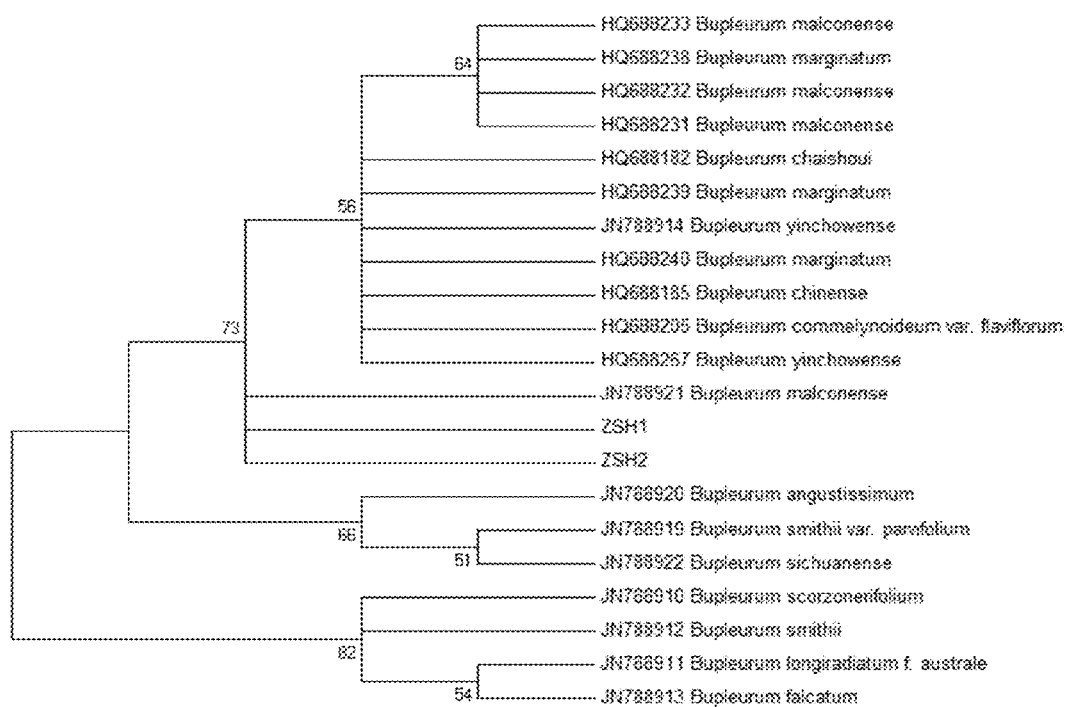
FIG. 1 shows NJ tree constructed by MEGA 4.0 based on psbA-trnH of 19 taxa of Dendrobium and one inspected species.

The dried roots of *Bupleurum malconense* are collected from Sichuan province of China. The plant material is identified and authenticated by Dr. Linfang Huang based on sequences of the plastid psbA-trn Hinter genetic region (FIG. 1)

Extraction and Isolation

Air-dried pieces of *Bupleurum malconense* root (500 g) are extracted for three times by percolation in petroleum ether (1 L); the supernatant is concentrated and collected as the petroleum ether (PE) extract. The residue is extracted for three times by reflux in 80% ethanol at 60° C.; the solution is concentrated to yield 80% ethanol extract. And then, the residue is further extracted by reflex in water (1 L) for three times to obtain the aqueous extract. Meanwhile, the 80% ethanol extract is dissolved in 200 mL of water in a separatory funnel, and then partitioned with ethyl acetate (200 mL×3). The upper and lower layers are collected to yield the ethyl acetate extract and ethanol extract, respectively. After freeze-drying (LABCONCO, Kansas, Mo., USA), different extracts are weighted, and respective percent composition is calculated, results being as followed: petroleum ether extract (0.8 g, 0.2%), ethyl acetate extract (4.7 g, 0.9%), ethanol extract (25.3 g, 5.1%), aqueous extract (24.2 g, 4.8%). All extracts are stored in −20° C. before use.

The petroleum ether extract is subjected onto silica gel column chromatography (300-400 mesh, DAVISIL, Germany) using petroleum ether/ethyl acetate (PE/EtOAc) of increasing polarity as an eluent. Pd-Ib, which is obtained from fraction 3 with 2.5% EtOAc in petroleum ether, is further purified using reverse phase HPLC (Waters system including a 2545 binary gradient module, a 2489 UV/Visible detector, a fraction collector III) on semi-preparative column Preparative RP-$C_{18}$ (Alltech Alltima-$C_{18}$, 250 mm×10.0 mm, 5 μm). The bioassay result and separation flow chart is showed in FIG. 2.

Anti-Inflammatory Bioassay (Quanti-Blue Assay)

RAW-Blue cells ($5×10^4$) are cultured in 96-well plate for 24 hours, and then treated with LPS (1 μg/mL) alone or together with test samples for 20 hours. Secreted embryonic alkaline phosphatase (SEAP) activity in the conditioned medium is determined using QUANTI-Blue medium following manufacturer's manual. Briefly, 100 μL samples are added to 200 μL of QUANTI-Blue medium and incubated at 37° C. for 15 to 30 minutes. Absorbance is measured at 620 nm using a micro-plate reader (Benchmark plus Bio-Red, CA, USA) and fold change in SEAP activity is calculated accordingly.

Cell Culture and Conditions

Raw-Blue cells are derived from RAW264.7 macrophages. Then the murine macrophage cell line of Raw-Blue cells is cultured in plastic dishes containing DMEM supplemented with 100 U/mL of penicillin, 100 μg/mL of streptomycin and 10% FBS in an incubator (5% $CO_2$) at 37° C. Cells are sub-cultured every 3 days at a dilution of 1:6.

Cell Viability Assays

Cells ($5×10^4$) are cultured in 96-well plates for 24 hours. Then cells are cultured with various concentrations of Pd-Ib (1.25, 2.5, 5, 10, 20, 40, 80, 100 μg/mL) for 24 hours. After that, 10 μL of 5 mg/mL MTT is added to each well, and the cells are cultured in the dark for 3 hours. The medium is then discarded, and 100 μL of dimethyl sulfoxide (DMSO) is added into each well. After 15 min incubation, the optical density at 570 nm is read by using a micro-plate reader to determine the cell viability.

Western Blot Analysis

After Raw-Blue cells are treated with LPS and Pd-Ib, whole cell extract is prepared with lysis buffer [1% Triton X-100, 0.1% SDS, 0.5% deoxycholate, 1 mM EDTA, 20 mM Tris (pH 7.4), 150 mM NaCl, 10 mM NaF, 1 mM $Na_3VO_4$, 0.1 mM phenylmethylsulfonyl fluoride and one protease inhibitor cocktail tablet (Roche, USA)]. Total protein concentration is measured using a protein assay kit, followed by centrifugation at 13,500 rpm for 15 minutes at 4° C., then 10-25 μg of protein from the supernatants is then separated on 10% sodium dodecylsulphate-polyacrylamide gel (SDS-PAGE) and transferred on to polyvinylidene difluoride membranes. After blocking with 5% skim milk powder in Tris-buffered saline-Tween (TBST; 50 mM Tris, 150 mM NaCl, pH 7.4; 0.01% Tween-20) for 1 hour at room temperature, the membrane is then incubated with primary antibody (1:5,000 dilution) in 5% skim milk in TBST overnight at 4° C. After washing with TBST (3×10 min), the membrane is incubated with secondary antibody (1:2,000 dilution) in 5% skim milk in TBST for 1 h at room temperature. The membrane is rewashed (TBST; 3×10 min), and the immune-reactive proteins are detected by enhanced chemiluminescence using X-ray film and ECL reagent. The protein bands are quantified by measuring the relative intensity compared to the control using Image J Software (version 4.1.7, NIH, USA).

Immunofluorescence Staining

Raw-Blue cells are cultured ($20×10^4$ cells/well) on glass coverslips and incubated for 24 hours. Cells are pretreated with various concentrations (5-20 μg/mL) of Pd-Ib for 2 hours. Then treated with LPS (1 μg/mL) for 20 hours. Subsequently, the coverslips are rinsed twice with PBS, and cells are fixed in 4% paraformaldehyde (PFA) in PBS at room temperature for 15 minutes. Cellular and nuclear membranes of the macrophages are permeabilized by treatment with 3% Triton X-100 in PBS for 15 minutes. After being blocked with 3% bovine serum albumin (BSA) in PBS for 1 hour, the cells is incubated with primary antibody in 3% BSA/PBS (1:500 dilution) at 4° C. overnight. After washing with PBS, the cells are incubated with the red-conjugated secondary antibody (1:500 dilution) in 3% BSA/PBS at room temperature for 1 hour and finally washed again for three time with PBS. Then, counter-staining is performed with DAPI (1:1,000 dilution) in 3% BSA/PBS nucleus with for 10 minutes. The cells are washed for three times with PBS, and then anti-fade mounting medium is added. Samples are observed under a fluorescence microscope.

Real-Time PCR Analysis

Raw-Blue cells are plated at $20×10^5$ cells/well in 12-well plate. After 24 hours of incubation, cells are pretreated with various concentrations (5-20 μg/mL) of Pd-Ib for 2 hours, followed by co-culturing with LPS (1 μg/mL) for 20 hours. Total RNA of Raw-Blue cells is extracted by Trizol reagent. Two micrograms (2 μg) of total RNA are reverse-transcribed with RT master mix to obtain cDNA. Real-time PCR is performed in a ViiA7 real-time PCR instrument (Applied Biosystems, Life Technologies, CA, USA) with the SYBR Green kit. A melting curve analysis is carried out after amplification to verify the accuracy of the amplicon. The comparative cycle of threshold ($\Delta\Delta C_T$) method of relative quantification is used to determine the fold-change in expression. Primer sequences for mRNA analysis of IL-1β, TNF-α, iNOS and β-Actin are described in Table 1.

TABLE 1

Sequence of primers used in real-time PCR

| Gene | Primer | Sequence (5'-3') | SEQ ID No. |
|---|---|---|---|
| iNOS | Sense | CACCTTGGAGTTCACCCAGT | 1 |
|  | Antisense | ACCACTCGTACTTGGGATGC | 2 |
| TNF-α | Sense | CTGTGAAGGGAATGGGTGTT | 3 |
|  | Antisense | GGTCACTGTCCCAGCATCTT | 4 |
| IL-1β | Sense | GCTGAAGGAGTTGCCAGAAA | 5 |
|  | Antisense | GTGCAAGTGACTCAGGGTGA | 6 |
| β-Actin | Sense | GGTGAAGGTCGGTGGAACG | 7 |
|  | Antisense | CTCGCTCCTGGAAGATGGTG | 8 |

Nitric Oxide Production Determination

Nitric oxide (NO) production is indirectly assessed by measuring the nitrite levels in the cultured medium determined by a colorimetric method based on the Griess reagent and sodium nitrite as a standard substance. The cells are pretreated with various concentrations of Pd-Ib (5-20 µg/mL). Two hours later, cells are incubated for another 20 hours in the presence of LPS (1 µg/mL) at 37° C. Then, 100 µL of each supernatant is mixed with the equal volume of Griess reagent. The samples are incubated at room temperature for 15 min. The optical densities are measured at 540 nm with a micro-plate reader and nitrite concentration is determined using a standard curve generated with known concentrations of sodium nitrite.

Animals 6-week-old male C57BL/6 mice weighing 18-20 g are purchased from the Laboratory Animal Services Center, the Chinese University of Hong Kong. The study protocols are approved by the committee for Care of Laboratory Animals in the School of Chinese Medicine at the Hong Kong Baptist University.

Induction of Chronic DSS Colitis and Treatment

The animals are divided into six groups (8-10 each group): control group (mice received drinking water and control diet), DSS-treated group (mice received 2.0% DSS in drinking and control diet), positive control group (mice received 2.0% DSS in drinking and ip, 300 mg/kg/day of sulfasalazine), Pd-Ib treatment groups will be given different dosed of Pd-Ib (mice received 2.0% DSS in drinking and i.p., 30, 60, or 120 mg/kg/day, respectively).

Figure 9:
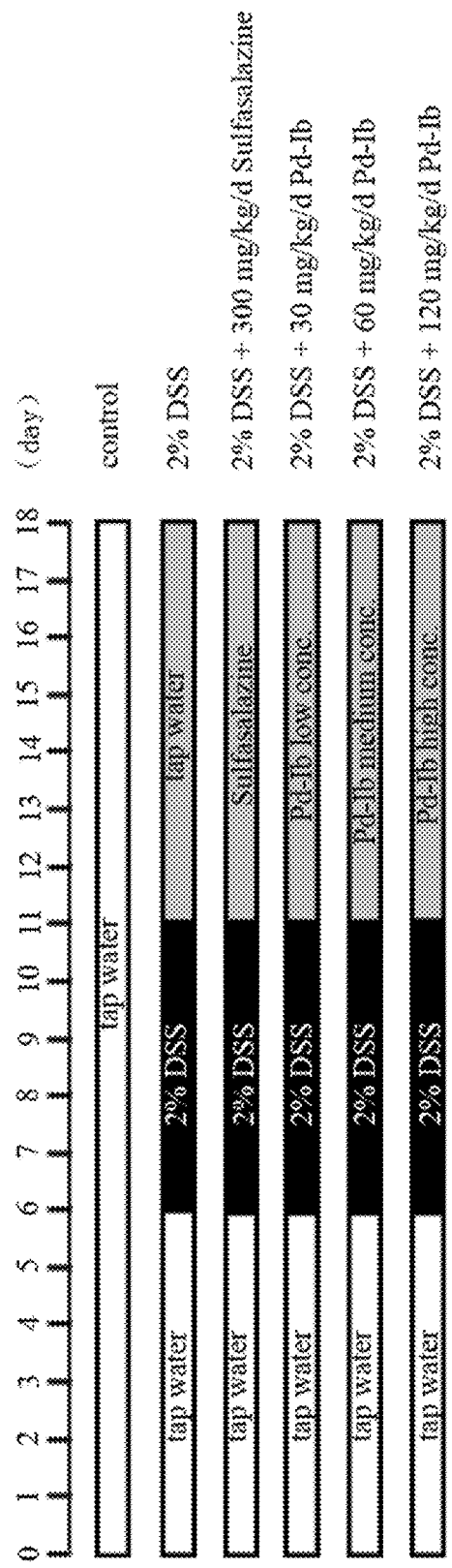
FIG. 9 shows the experimental design of animal model with DSS-induced colitis and treated with different concentrations of Pd-Ib or Sulfasalazine.

As depicted in experiment design shown in FIG. 9, the mice are given tap water for 6 days, and then be divided into 6 groups. DSS is dissolved in distilled water at a concentration of 2% (w/v) and administered to the mice. The first day and the last day of DSS treatment are designated as day 7 and day 11, respectively. Mice are marked and checked daily for body weight. On day 12, body weight, stool consistency, and gross bleeding of each mouse are assessed, and animals showing body weight loss, diarrhea, and bleeding are selected for further analysis. All colitis mice are then interventions once daily for seven days, with eight mice in each group. The DSS model group is administered with tap water as negative control; while sulfasalazine is given as positive control (i.p., 300 mg/kg/day) and Pd-Ib treatment groups are given different doses of Pd-Ib (i.p., 30, 60, or 120 mg/kg/day, respectively). In parallel, a vehicle control group is also set up to receive drinking tap water without DSS throughout the entire experimental period. On day 19, after the mice are killed under anesthesia induced by pentobarbital sodium (i.p., 0.65 g/kg), the length of the large intestine is measured. All portions are stored at −80° C. for biochemical assays.

Evaluation of Disease Activity Index (Dai)

The DAI is determined by scoring changes in the body weight, diarrhea, colon length, and bleeding. Each score is given in Table 2. In brief, body weight, stool consistency, colon length and bleeding in the stool are monitored daily for determination of DAI. At the end of the experiment, mice are killed, and the colon is dissected from each mouse, and the length of which is measured from the ileocecal junction to the anal verge.

TABLE 2

Disease Activity Index Scores Based on Disease Marker Intensities

| Score | Body weight loss (%) | Diarrhea (stool consistency) | Rectal bleeding |
|---|---|---|---|
| 0 | None | 0 | negative |
| 1 | 1-5 | 1 | faintly blue |
| 2 | 6-10 | 2 | moderately blue |
| 3 | 10-15 | 3 | dark blue |
| 4 | >15 | 4 | dark blue, prolapse |

Histological Analysis

The colons are opened longitudinally, gently washed with ice-cold PBS, fixed in 4% paraformaldehyde overnight, and embedded in paraffin. Five-micro-meter sections are stained with hematoxylin/eosin according to a standard procedure to evaluate colonic damage. The histological scoring system is shown in Table 3.

TABLE 3

Histological Scoring System for DSS-Induced Colitis
Scoring of severity of histological damage

| Feature | Score | Description |
|---|---|---|
| Severity of inflammation | 0 | none |
|  | 1 | mild |
|  | 2 | moderate |
|  | 3 | severe |
| Extent of inflammation | 0 | none |
|  | 1 | mucosa |
|  | 2 | mucosa and submucosa |
|  | 3 | transmural |
| Crypt damage | 0 | none |
|  | 1 | ⅓ damaged |
|  | 2 | ⅔ damaged |
|  | 3 | crypt loss by surface epithelium present |
|  | 4 | both crypt and surface epithelium lost |

Determination of Neutrophil Infiltration in Colon Tissue (MPO Assay)

Myeloperoxidase (MPO) is an enzyme mainly released by neutrophil, and its activity is directly associated with the severity of inflammation in a given tissue. In this example, MPO activity is measured as described in our previous study. Briefly, the colon tissues kept at −80° C. are weighed and homogenized in 0.5% hexadecyltrimethylammonium bromide 1 mL per 100 mg of colon tissue. The homogenates are centrifuged at 19 000 rpm at 4° C. for 15 min. Aliquots of 80 iL supernatant are mixed with 120 µL potassium phosphate buffer (50 mmol, pH 6.0) with 0.0005% o-dianisidine dihydrochloride and 0.1% hydrogen peroxide. Changes in optical density are measured at 460 nm at room temperature (25° C.). MPO activity is calculated from the rate of optical density changes and one unit of MPO activity is defined as the amount of enzyme present that produced a change in optical density of 1.0 U/min at 25° C. in the final reaction volume. The results are normalized to the wet weight of colon tissue and quantified as units/mg tissue.

Enzyme-Linked Immunosorbent Assay (ELISA) FRO Cytokines Quantification

Colon levels of cytokines are assayed using commercially available ELISA kits. Briefly, colon samples are homogenized in phosphate buffer containing 0.05% Tween-20, 0.1 mM phenylmethylsulfonyl fluoride, 0.1 mM benzethonium chloride, 10 mM EDTA, and 20 IU aprotinin A. The homogenates are centrifuged at 16000 g at 4° C. for 15 min, and the supernatants are collected for the determination of levels of the cytokines, IL-6, IL-4, TNF-α, and IFN-γ, according to the manufacturer's protocols. The amount of protein in each sample is measured by the Bradford method, using bovine serum albumin as a standard. The levels of each cytokine are evaluated in each sample and expressed in μg/mL.

Statistical Analysis

Data are expressed in terms of mean±SEM. Variables between groups are compared using one-way ANOVA, followed by Duncan's new multiple range tests. GraphPad Prism 5.0 software (GraphPad Software Inc., San Diego, Calif., USA) is used for all calculations, and $P<0.05$ is considered as statistically significant.

Result and Discussion

Bioassay-Guided Isolation and Structural Identification

Figure 2:
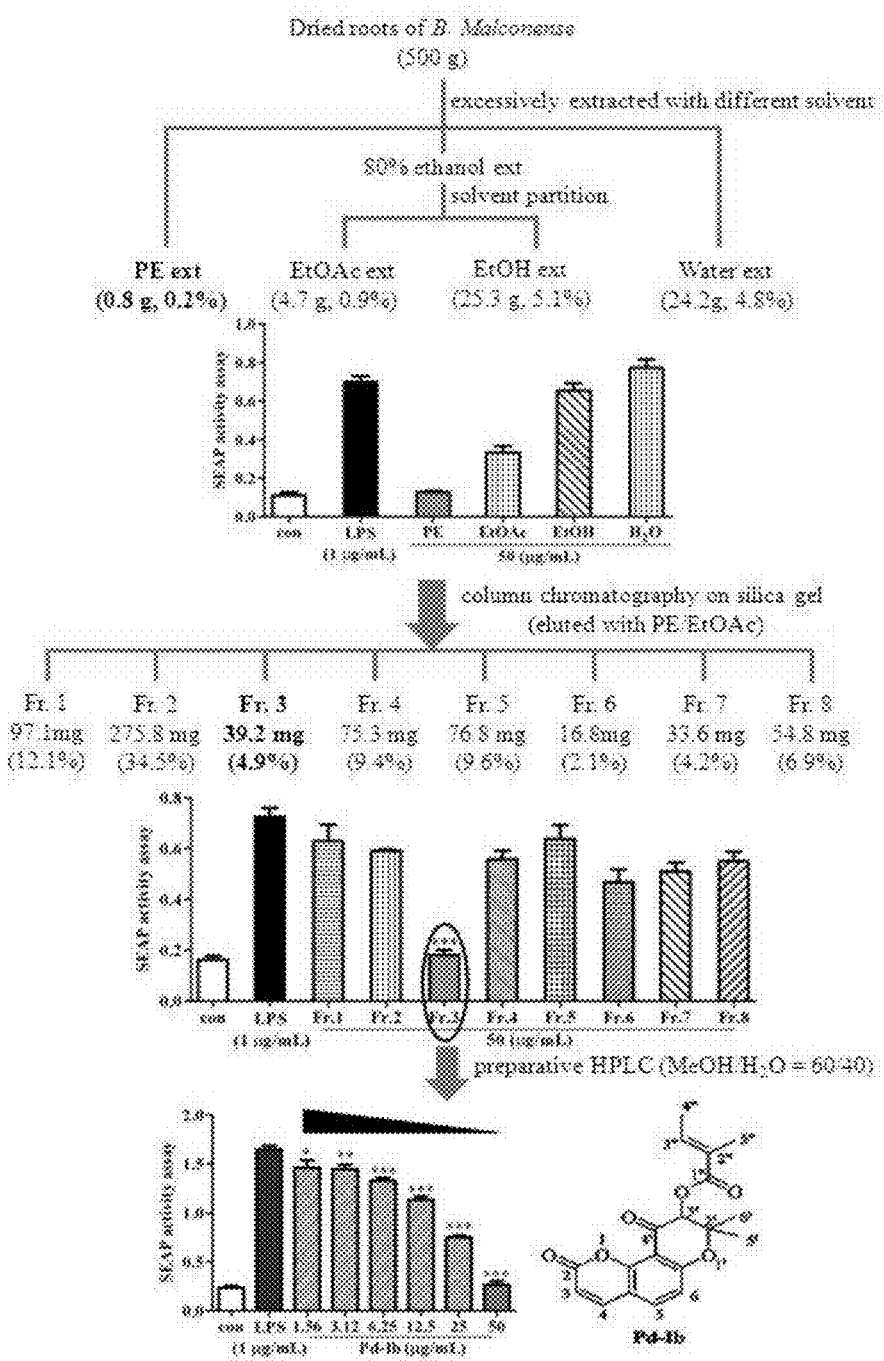
FIG. 2 shows flow chart of bioassay-guided isolation anti-inflammatory compound of *Bupleurum malconense*. The effect of test samples on inhibited SEAP activity in LPS-stimulated RAW-Blue cells. *P<0.05, P<0.01 and *P<0.001 are compared with LPS-alone group. "PE ext" stands for petroleum ether extract, "EtOAc" stands for ethyl acetate extract, "EtOH" stands for ethanol extract, "$H_2O$" stands for water extract, "Fr" stands for fraction.
Figure 3:
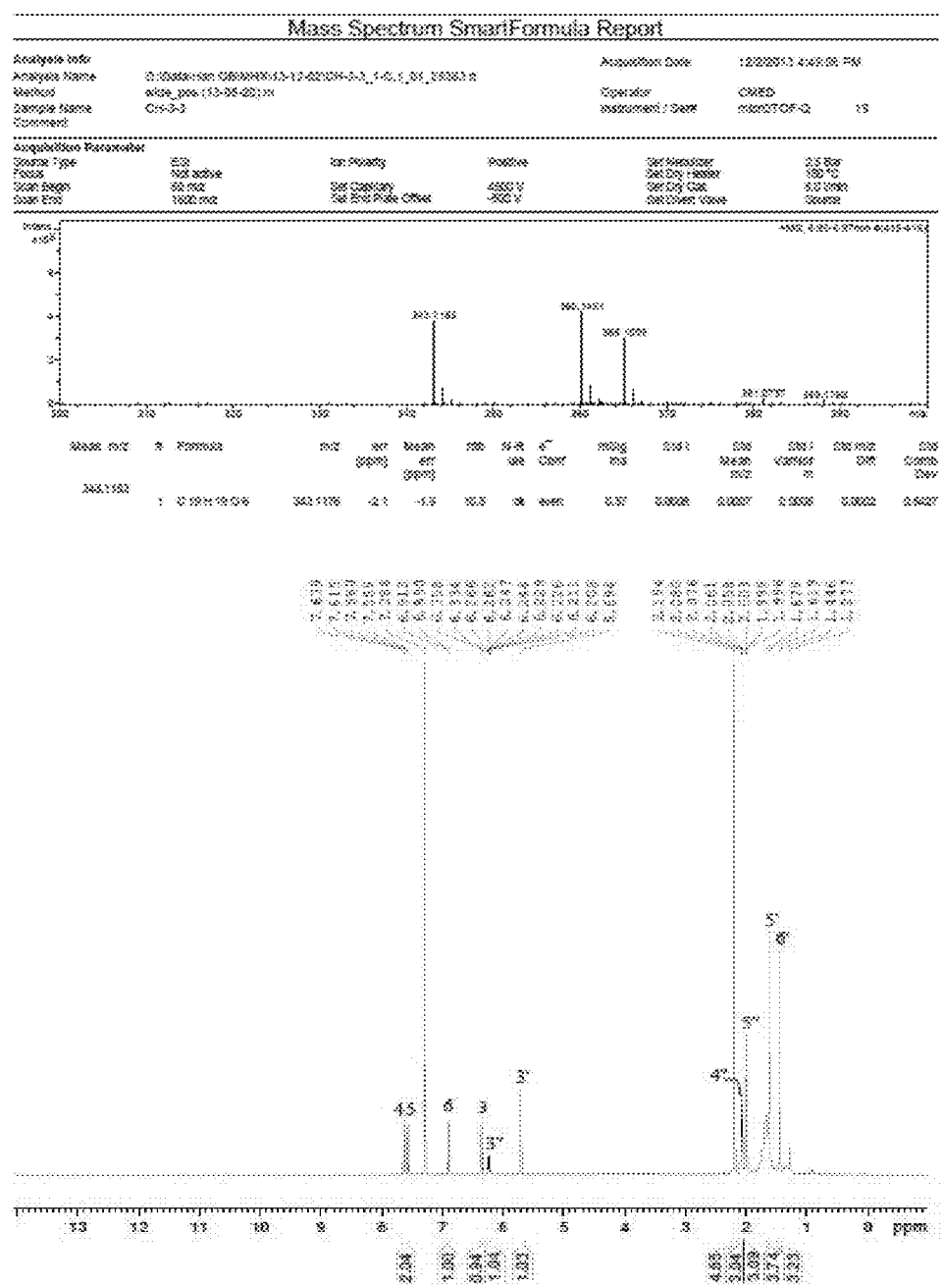
FIG. 3 shows HR-ESI-MS and $^1$H NMR spectrum of Pd-Ib

As shown in FIG. 2, PE extract exerts significant inhibitory effect of SEAP activity compared with LPS group (18.19±0.967%). To advance in the search for anti-inflammatory compounds, the PE extract is subjected to silica gel chromatography using PE/EtOAc as an eluent and 8 fractions are collected. Since the SEAP activity is significantly inhibited by Fr.3 (30.661±2.546%), further purification is carried out to isolate one pure compound. This compound, which dose-dependently inhibits the SEAP activity ($IC_{50}$=22.53 μg/mL) in LPS-stimulated macrophages, is determined to be (+)-3'-Angeloyloxy-4'-keto-3',4'-dihydroseselin (Pd-Ib) by analysis of its HR-MS (MicrOToF-Q Bruker mass spectrometer equipped with Acquity Waters ultra-high performance liquid chromatography) and NMR spectra (Bruker 400 Hz NMR spectrometer). The spectral data (FIG. 3) are identical to those reported in Wang X. B., et. al., (+)-(3'R)-angeloyloxy-4'-keto-3',4'-dihydroseselin (Pd-Ib). Acta. *Crystallographica* 2006, E62, 2505-07; and Liu, R. et al., Preparative isolation and purification of coumarins from *Peucedanum praeruptorum* Dunn by high-speed counter-current chromatography. *J. Chromatogr. A*. 2004, 1057, 89-94.

(+)-3'-Angeloyloxy-4'-keto-3',4'-dihydroseselin (Pd-Ib) Yield 2.38 mg, white powder (MeOH). HR-ESI$^+$-MS: m/z 342.1183 [M+H]$^+$ (calcd for $C_{19}H_{18}O_6$, 342.1182). $^1$H-NMR (CDCl$_3$, 400 MHz) ä: 6.35 (1H, d, J=9.6 Hz, H-3), 7.63 (1H, d, J=9.6 Hz, H-4), 7.57 (1H, d, J=8.4 Hz, H-5), 6.90 (1H, d, J=8.8 Hz, H-6), 5.69 (1H, s, J=4.8 Hz, H-3'), 1.62 (3H, s, 5'-CH$_3$), 1.45 (3H, s, 5'-CH$_3$), 6.25 (1H, q, J=7.5 Hz, H-3"), 2.07 (3H, d, J=8.8 Hz, 4"-CH$_3$), 2.00 (3H, s, 5"-CH$_3$).

Cytotoxity of Pd-Ib on Raw-Blue Cells

Figure 4:
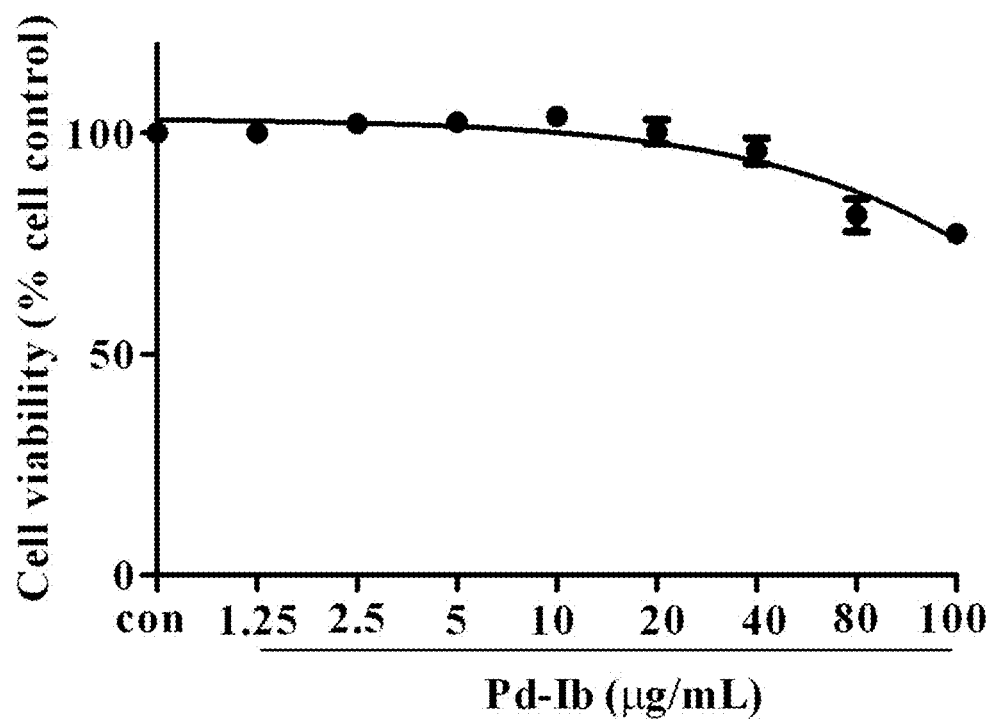
FIG. 4 shows effect of Pd-Ib on the viability of LPS-stimulated RAW-Blue cells. Cells are cultured for 24 hours in the presence of Pd-Ib at the concentrations indicated, from 1.25-100 μg/mL. Cell viability is assessed using MTT assay. Data are derived from three independent experiments and presented as mean±SEM. "con" stands for the vehicle control group.

Prior to evaluating the anti-inflammatory activity of Pd-Ib, the cytotoxic effect of Pd-Ib on Raw-Blue cells is tested with the MTT assay. As shown in FIG. 4, the Pd-Ib of the present invention does not exhibit cytotoxic effect at dosages ranging from 1.56 to 20 μg/mL, while cell viability is reduced when macrophages are treated with Pd-Ib at doses of 40, 80, and 100 μg/mL.

Figure 5:
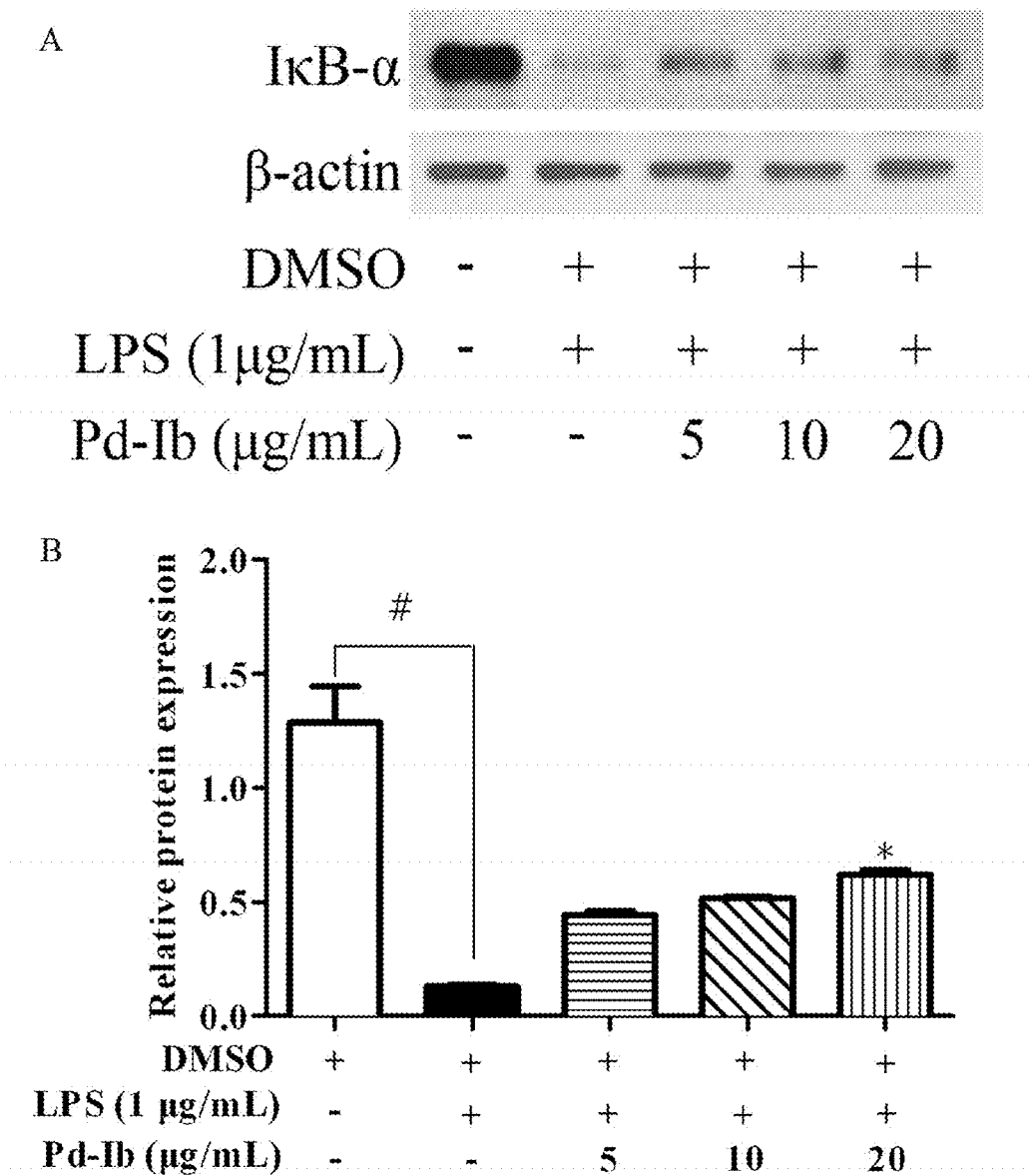
FIG. 5 shows inhibition effect of Pd-Ib on the IκB-α degradation in LPS-stimulated RAW-Blue cells. After macrophages are treated with 1 μg/mL of LPS in absence or presence various concentrations of Pd-Ib (5, 10, 20 μg/mL) for 20 h, the protein level of IκB-α is determined by Western blotting, β-actin is used as a quantity control: (A) shows representative image of Western blotting. (B) shows protein levels of IκB-α is calculated with Image J software. Data are derived from three independent experiments and presented as mean±SEM. #Compared with control group. *P<0.05 is compared with LPS-alone group.

Pd-Ib Inhibits the Nuclear Translocation of NF-KB and Decreases Degradation of IKB-α in LPS-Stimulated Raw-Blue Cells The SEAP activity in the supernatants of LPS-stimulated RAW-Blue cells reflects the activation of NF-κB. The inhibition of the NF-κB activation can associate with mitigation of colon inflammation responses and apoptosis of intestinal epithelial cells in DSS mouse model. Western blotting and immunofluorescence analysis are performed to determine whether Pd-Ib depressed NF-κB activation. The effect of Pd-Ib on LPS-induced IκB-α degradation is investigated to examine the molecular mechanisms by which Pd-Ib inhibits NF-κB transcriptional activity. As shown in FIG. 5, Pd-Ib inhibits IκB-α degradation in a dose-dependent manner compared to the LPS-stimulated macrophage.

Figure 6:
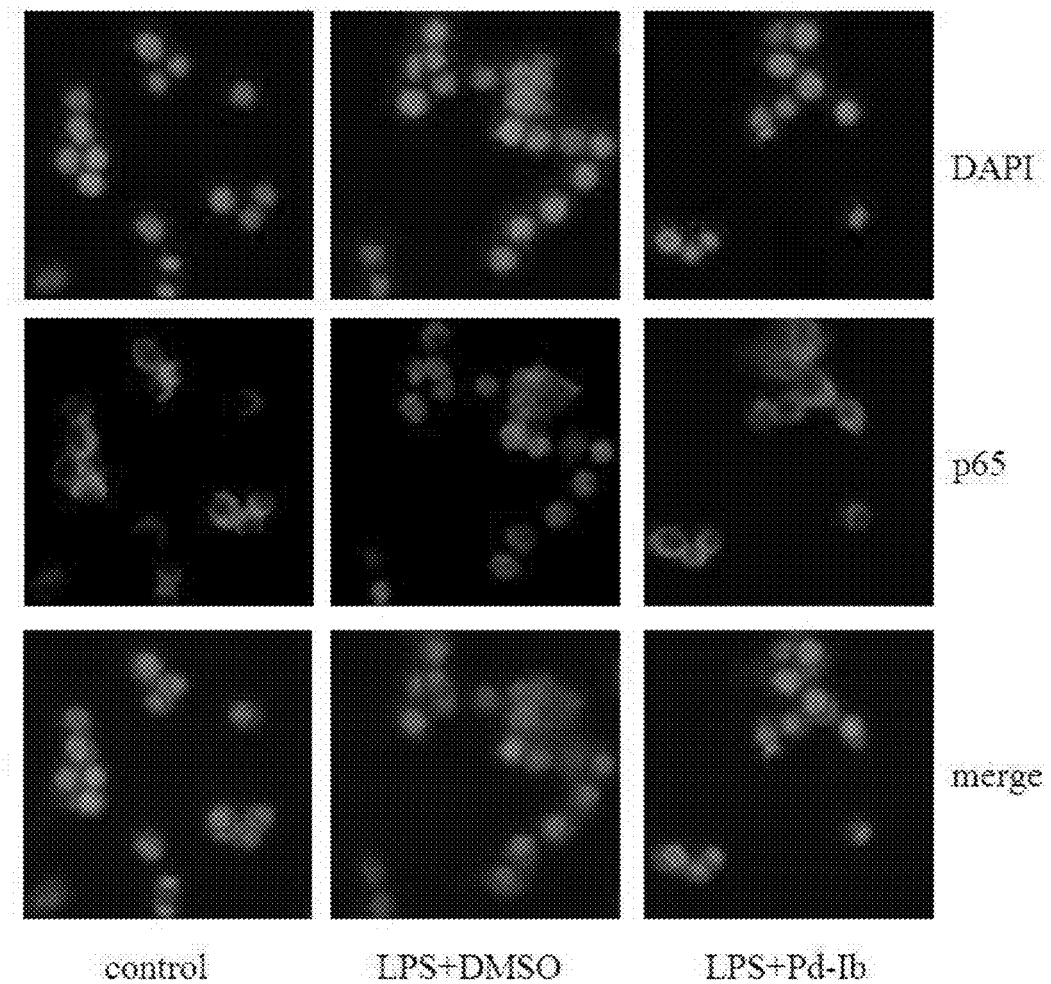
FIG. 6 shows effect of Pd-Ib on nuclear translocation of NF-κB as evaluated by immunofluorescence. Data are derived from three independent experiments. Original magnification, 40×.

The immunofluorescence result shows that a low level of p65 activity is observed in the control group. It also revealed that treatment with Pd-Ib significantly inhibits the p65 nuclear translocation compared to the LPS-stimulated macrophage (FIG. 6).

Figure 7:
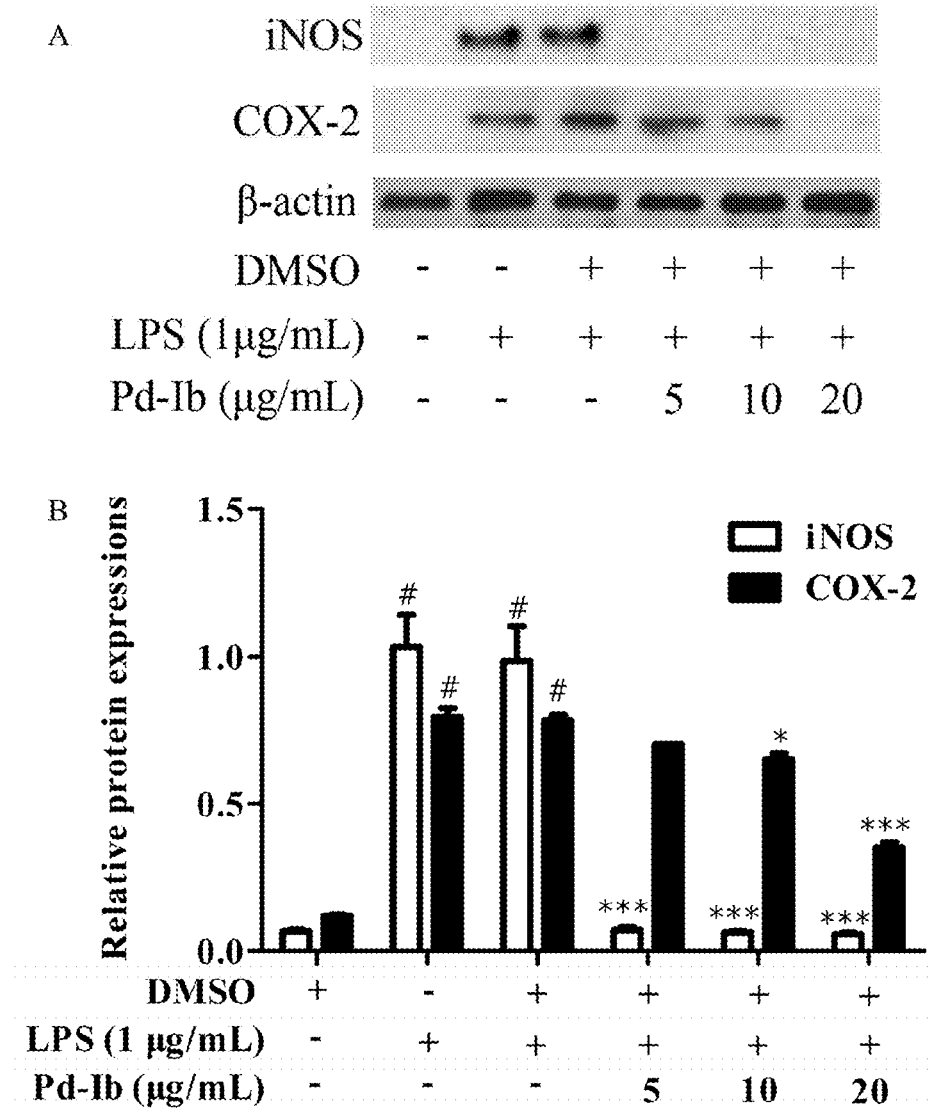
FIG. 7 shows inhibitory effects of Pd-Ib on the iNOS and COX-2 in LPS-stimulated RAW-Blue cells. After macrophages are treated with 1 μg/mL of LPS in absence or presence various concentrations of Pd-Ib (5, 10, 20 μg/mL) for 20 h, the protein levels of iNOS and COX-2 are determined by Western blotting, β-actin is used as a quantity control: (A) shows representative images of Western blotting; (B) shows protein levels of iNOS and COX-2 are calculated with Image J software. Data are derived from three independent experiments and presented as mean±SEM. #Compared with control group. *P<0.05, P<0.01 and *P<0.001 are compared with LPS-alone group.

Pd-Ib Suppresses the Expressions of iNOS and Cox-2 in LPS-Stimulated Raw-Blue Cell COX-2 and iNOS are the important enzymes that mediate inflammatory pathways. High expression levels will cause intestinal inflammation with motility dysfunction (Tajima et al., "EP2 and EP4 receptors on muscularis resident macrophages mediate LPS-induced intestinal dysmotility via iNOS upregulation through cAMP/ERK signals", *Am J Physiol Gastrointest Liver Physiol* 2012, 302: G524-534). Western blotting analysis shows that Pd-Ib strongly down-regulates iNOS and COX-2 protein levels in a dose-dependent manner (FIG. 7A). The intensity of protein bands are analyzed and the results are shown in FIG. 7B.

Figure 8:
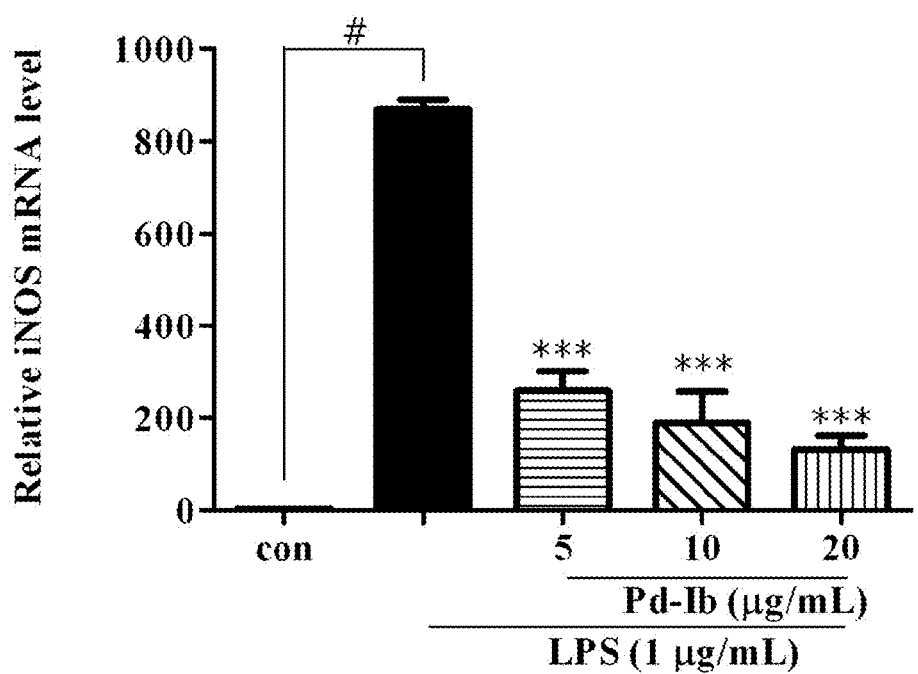
FIG. 8 shows effects of pro-inflammatory factors release and nitric oxide production in LPS-stimulated RAW-Blue cells. After macrophages are treated with 1 μg/mL of LPS in absence or presence various concentrations of Pd-Ib (5, 10, 20 μg/mL) for 20 hours, the mRNA levels of iNOS (A), TNF-α (B) and IL-1β (C) are determined by real time PCR, while the production of NO (D) is determined by Griess reagent. Data are derived from three independent experiments and presented as mean±SEM, "con" stands for the vehicle control group. #Compared with control group. *P<0.05, P<0.01 and *P<0.001 are compared with LPS-alone group.
Figure 8:
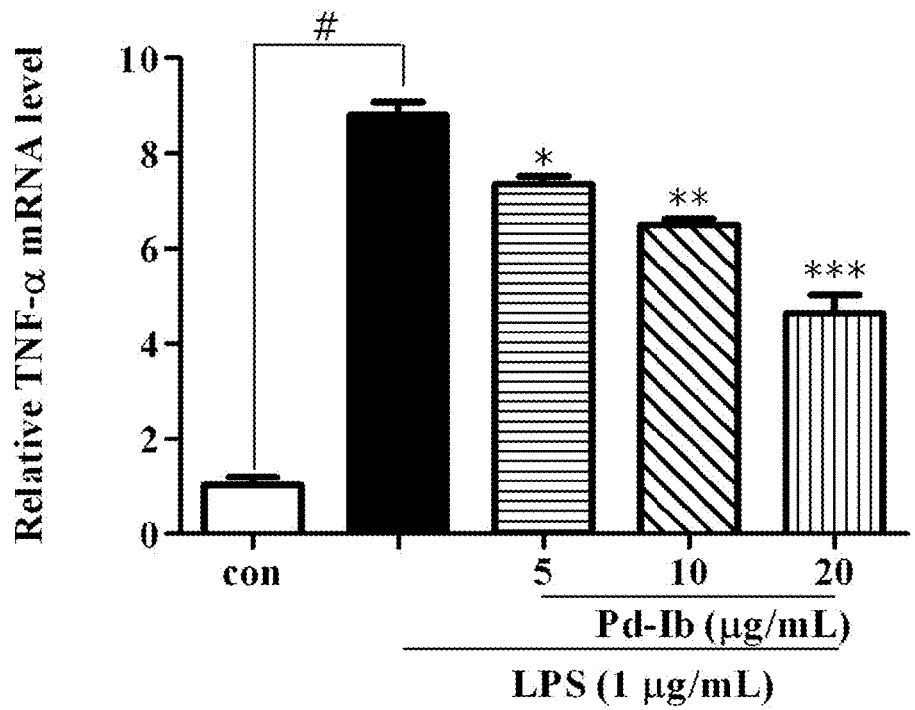

Meanwhile, the effect of Pd-Ib on mRNA expression of iNOS is investigated in LPS-stimulated Raw-Blue cells. As shown in FIG. 8A, Pd-Ib also remarkedly inhibits the mRNA level of iNOS in a dose-dependent manner. These results confirm that Pd-Ib plays a key role in the inhibition of protein and gene levels of iNOS.

Pd-Ib Inhibits the mRNA Expressions of TNF-α and IL-1β in LPS-Stimulated Raw-Blue Cells High levels of pro-inflammatory cytokines are associated with pain, lung inflammation and rheumatoid arthritis (DeVon et al., "The association of pain with protein inflammatory biomarkers: a review of the literature", *Nurs Res* 2014, 63: 51-62; Lim et al., "Inhibition of proinflammatory cytokine generation in lung inflammation by the leaves of *Perilla frutescens* and its constituents", *Biomol Ther* (*Seoul*) 2014, 22: 62-67; Yang et al, "Inhibitory effect of *litchi* (*Litchi chinensis* Sonn.) flower on lipopolysaccharide-induced expression of proinflammatory mediators in RAW264.7 cells through NF-κB, ERK, and JAK2/STAT3 inactivation", *J Agric Food Chem* 2014, 62: 3458-3465). TNF-α and IL-1β are produced in the early stage of inflammatory response and play important roles in varies inflammatory cascades. Real-time PCR experiments are performed to examine the expression of pro-inflammatory cytokines following LPS treatment. As shown in FIG. 8B and FIG. 8C. Pd-Ib could inhibit the mRNA expressions of TNF-α and IL-1β in a dose-dependent manner, while LPS stimulation of macrophages causes an increase in their expressions.

PD-IB Inhibits Nitric Oxide (NO) Production in LPS-Stimulated Raw-Blue Cells

Generally, nitric oxide (NO) is a critical mediator of a variety of biological functions; however, production of excessive amounts of NO leads to inflammatory responses or tissue injury (Aktan F: iNOS-mediated nitric oxide production and its regulation. *Life Sci* 2004, 75: 639-653). The effect of Pd-Ib on NO production is investigated using Griess reagent. As shown in FIG. 8D, stimulation with LPS results in a significant increase in NO production compared with the control group while treatment with Pd-Ib at 5, 10, 20 μg/mL led to 17.64±2.96%, 29.82±1.34% and 55.45±1.15% inhibition of NO production, respectively.

In the present invention, a combination of chromatographic techniques for bioassay-guided isolation of anti-inflammatory compounds from *Bupleurum malconense* is provided. Pd-Ib is isolated from *Bupleurum malconense* for the first time, and it is found to have excellent anti-inflammatory activities. To date, little is known about the role of Pd-Ib in anti-inflammatory effects. It is demonstrated that Pd-Ib suppresses LPS-induced inflammatory responses in macrophage Raw-Blue cells.

The QUANTI-Blue assay results show that, Pd-Ib exerts anti-inflammatory effects through inhibition of SEAP activity. SEAP is a widely use reporter gene widely used to screen immune-pharmacological activity upon the activation of NF-κB and activator protein 1 (AP-1). When Raw-Blue cells are stimulated with LPS, IκB-α which is the inhibitory subunit of NF-κB, is rapidly phosphorylated Subsequently, NF-κB releases from the IκB-α subunit and translocates to the nucleus, where it increases the expression of the genes for many cytokines, enzymes and adhesion molecules. In the present invention, Pd-Ib is shown to significantly inhibit LPS-stimulated degradation of IκB-α and nuclear translocation of NF-κB.

Increased expression of COX-2 and iNOS, two key factors regulated by NF-κB, are reflected in an increased amount of NO in the colons of patients with active ulcerative colitis. Pd-Ib significantly inhibits the protein expression of COX-2 and iNOS, resulting in the reduction of NO in activated macrophages. The results also suggest that Pd-Ib is able to down-regulate the protein levels of iNOS by reducing the mRNA expression of iNOS.

The pro-inflammatory cytokines, including TNF-α and IL-1β, play an important role in the mediation of inflammatory processes. When those mediators are overproduced, they lead to various diseases. Thus, the inhibition of pro-inflammatory cytokines release may help attenuate the inflammatory response. The result in the present invention indicates that Pd-Ib could significantly down-regulate the mRNAs expression of TNF-α and IL-1β in a dose-dependent manner.

In summary, the present invention firstly reports the isolation of Pd-Ib from *Bupleurum malconense* and demonstrates Pd-Ib's anti-inflammatory effect in LPS-stimulated macrophages. This beneficial effect in alleviating the inflammatory response of TNF-α, IL-1β, NO and iNOS in LPS-stimulated Raw-Blue cells can be caused by down-regulating iNOS and COX-2 protein expression via the blockade of NF-κB activation. It is concluded that the petroleum ether extract of *Bupleurum malconense* is efficacious for the treatment of inflammatory disease; meanwhile, Pd-Ib could be a potential anti-inflammatory agent.

These results give an indication to find whether the Pd-Ib will be efficacious for the treatment of inflammatory disease, such as ulcerative colitis (UC) and Crohn's disease (CD).

Thus, the present invention will be undertaken to evaluate the possible effect of Pd-Ib in a model of chronic DSS-induced colitis in mice with the aid of macroscopic and histological analyses, to determine the key pro-inflammatory mediators involved in IBD development.

DSS-induced colitis is one of the most common models with several characteristics resembling human ulcerative colitis. In this example, mice exposed to DSS drinking water develop typical symptoms of clinical colitis, including body weight loss, diarrhea, rectal bleeding and diarrhea. As shown in FIG. 10A, mice in groups treated with Pd-Ib at 120 mg/kg/day recover the body weight loss significantly compared with that of DSS model group after 10 days (p<0.05). However, Pd-Ib is mildly effective in preventing body weight loss at 30 mg/kg/day and 60 mg/kg/day. Pd-Ib also leads to clinical improvement of DSS-induced colitis, as reflected in the DAI, colon length and the histological disease score. Overall, the DAI score, which is 0 in control mice, is significantly lower in mice treated with Pd-Ib at 120 mg/kg/day than untreated mice (FIG. 10B, p<0.05). In addition, as another important symptomatic parameter in DSS-induced colitis, shortening of colon length, is rectified after administration with Pd-Ib at indicated concentration levels in a dose-dependent manner (FIG. 10C and FIG. 10D, p<0.05, p<0.001). With reference to teaching by Regan-Shaw et al. (2007), effective human dose can be calculated based on the following equation:

$$D_{human} = D_{mouse} \times k (k=0.081)$$

where $D_{human}$ is equivalent dosage for adult human; $D_{mouse}$ is dosage for mouse Based on the findings in FIG. 10, the lower dosage of Pd-Ib for mouse is 30 mg/kg/day; medium dosage for mouse is 60 mg/kg/day; higher dosage for mouse is 120 mg/kg/day, in which the dosage of 120 mg/kg/day for mouse is most effective in treating inflammation or inflammatory diseases in terms of preventing weight loss in the mouse model, having the lower DAI score which is comparable to untreated mice, preventing reduction in colon length, and preventing rectal bleeding found in stool.

By calculation using the equation and coefficient taught by Regan-Shaw et al., the lower, medium and higher dosages of Pd-Ib for human are as follows:

$$\text{Lower dosage of Pd-Ib for human} = D_{mouse} \times k = 30 \text{ mg/kg/day} \times 0.081 = 2.43 \text{ mg/kg/day};$$

$$\text{Medium dosage for human} = D_{mouse} \times k = 60 \text{ mg/kg/day} \times 0.081 = 4.86 \text{ mg/kg/day};$$

$$\text{Higher dosage for human} = D_{mouse} \times k = 120 \text{ mg/kg/day} \times 0.081 = 9.72 \text{ mg/kg/day}.$$

Figure 10:
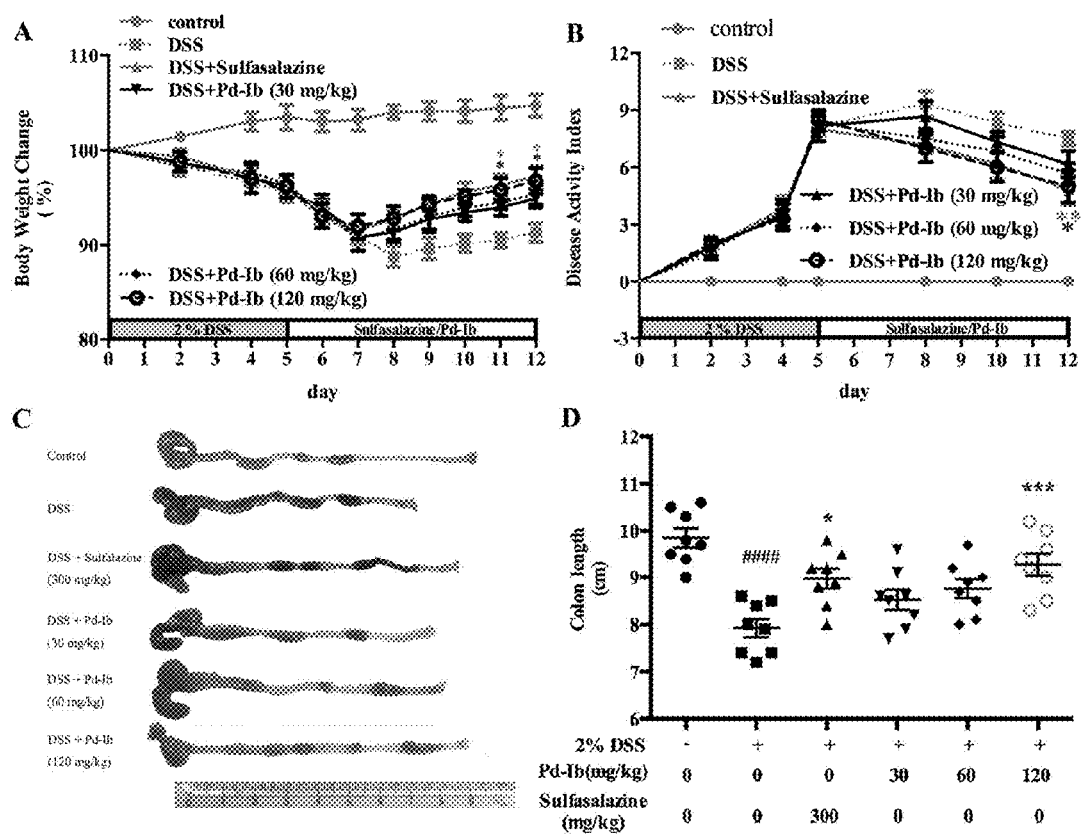
FIG. 10 shows the effects of Pd-Ib on body weight change (A), disease activity index (B), and colon length (C and D) of mice with DSS-induced colitis.
Figure 11:
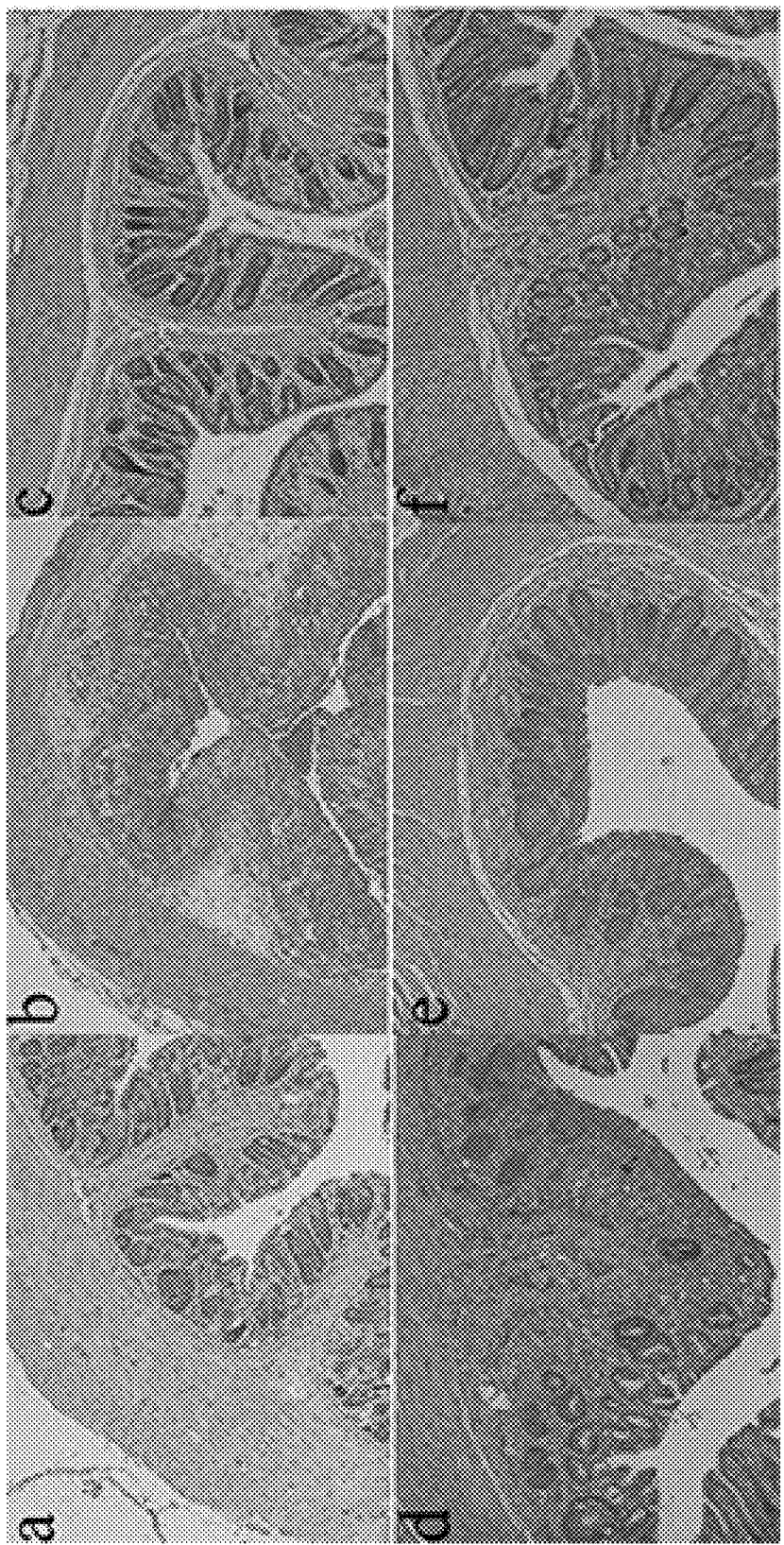
FIG. 11 shows effects of Pd-Ib on histological manifestation in DSS-induced chronic colitis in mice: (a) control; (b) 2% DSS-treated; (c) 2% DSS+sulfasalazine at 300 mg/kg/day for seven consecutive days; (d) 2% DSS+Pd-Ib at 30 mg/kg/day for seven consecutive days; (e) 2% DSS+Pd-Ib at 60 mg/kg/day for seven consecutive days; (f) 2% DSS+Pd-Ib at 120 mg/kg/day for seven consecutive days.

Histological analysis of the samples from the DSS-induced mice showed typical inflammatory changes in colon architecture including mucosal ulceration, crypt damage, edema, and cell infiltration into mucosal tissue. Pd-Ib exhibited a clinical improvement of DSS-induced colitis, as reflected in the histological manifestation and DAI (FIGS. 10 and 11). Colon tissue sections from mice fed with Pd-Ib exhibited far fewer infiltration cells, a significantly lower degree of mucosal injury, and less edema.

Colitis is induced in all groups except the control group. Pd-Ib and sulfasalazine are administered to mice from day 6 to day 12. The change in body weight is taken as the difference between the body weight before induction of colitis and that immediately before sacrifice on day 13. The DAI score is determined by combining scores of (i) body weight loss, (ii) stool consistency, and (iii) stool bleeding. On day 13, the mice are sacrificed, and the colon lengths are measured. Data are expressed as mean±SEM, n=8 ([####]p<0.001, compared with the control group; *p<0.05, p<0.01, *p<0.001, compared with DSS model group).

Hematoxylin and eosin staining images of representative colons are shown at magnifications of 10× (a, control group; b, DSS model group; c, DSS plus sulfasalazine 300 mg/kg/day group; d, DSS plus Pd-Ib 30 mg/kg/day group; e, DSS plus Pd-Ib 60 mg/kg/day group; f, DSS plus Pd-Ib 120 mg/kg/day group).

In FIG. 11, the present invention shows that DSS treatment (FIG. 11b) can cause typical inflammatory changes in colon architecture, including mucosal ulceration, crypt damage, edema, and cell infiltration into mucosal tissue, which compared with the control group (FIG. 11a). As shown in FIG. 11c, the sulfasalazine treatment group can significantly decrease the damage of colon tissues. Compared with the FIG. 11b, Pd-Ib exhibits a clinical improvement in DSS-induced colitis, which is reflected in the DAI score. Colon tissue sections from mice treated with Pd-Ib exhibits far fewer infiltrating cells, a significantly lower degree of mucosal injury, and less edema at different dosage treatment (as shown in FIGS. 11d, e, and f).

Figure 12:
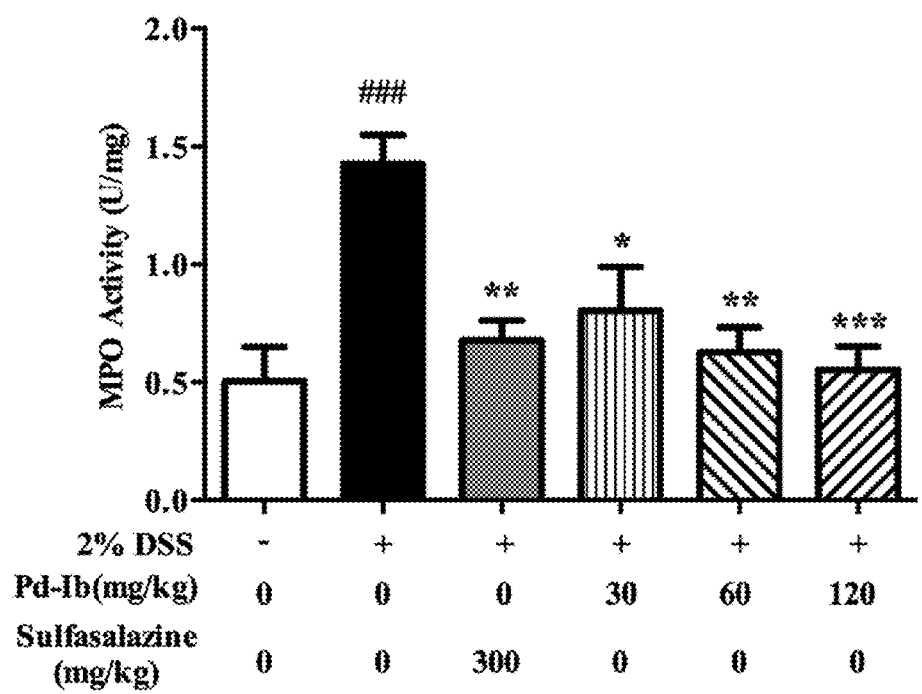
FIG. 12 shows effects of Pd-Ib on suppress myeloperoxidase (MPO) activity in the colon of mice with DSS-induced colitis.

During mucosal inflammation, a complex array of inflammatory signaling involving prostaglandins and cytokine production impairs intestinal epithelial function and leads to the recruitment of inflammatory cells to the site of injury. Previous studies have shown that neutrophil infiltration into inflamed tissue can facilitate the formation of potent cytotoxic oxidants to induce colon tissue damage through the enzyme myeloperoxidase (MPO). The present invention shows that Pd-Ib suppresses MPO activity significantly in the DSS-induced colitic mice, and similar results are observed in mice administrated with a positive control agent sulfasalazine (300 mg/kg/day) (FIG. 12).

Colitis is induced in all groups except the control group. Pd-Ib and sulfasalazine are administered to mice from day 6 to day 12. On day 13, the mice are sacrificed, and MPO activity is determined in colon homogenates. Data are expressed as mean±SEM, n=8 (*p<0.05, p<0.01, *p<0.001, compared with DSS model group).

Figure 13:
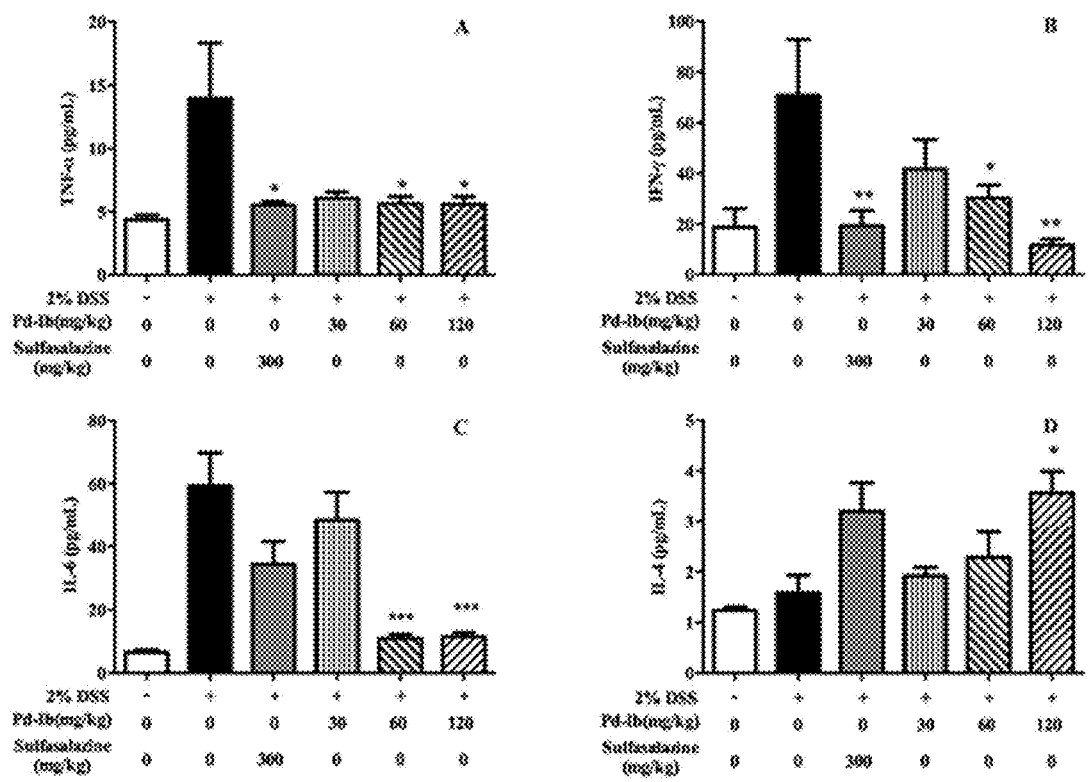
FIG. 13 shows the effects of Pd-Ib on the production of cytokines in colon tissue of animals with DSS-induced colitis: (A) TNF-α levels; (B) IFN-γ levels. (C) IL-6 levels; (D) IL-4 levels.

It is well accepted that imbalances between pro-inflammatory cytokines, such as TNF-α, IFN-γ, IL-1β and IL-6, and anti-inflammatory cytokines, including IL-10, IL-4, IL-5 are involved in regulated the inflammatory status. In the present invention, it is found that DSS treatment causes a prominent increase of TNF-α, IFN-γ, and IL-6 in the colon tissues of mice. Interestingly, Pd-Ib greatly reduces the production of TNF-α, IFN-γ, and IL-6 compared with the DSS treatment group, whereas significant effect on the production of IL-4 in a dose-dependent manner is observed (FIG. 13). The results indicate that Pd-Ib could alleviate the DSS-induced inflammation which partially contributes to the observed reduction of the pro-inflammatory cytokines TNF-α, IFN-γ, and IL-6 and increase in IL-4 secreted in colon of DSS-treated mice.

Colitis is induced in all groups except the control group. Pd-Ib and sulfasalazine are administered to mice from day 6 to day 12. On day 13, the mice are sacrificed, Data are expressed as mean±SEM, n=8 (*p<0.05, p<0.01, *p<0.001, compared with DSS model group).

It is well accepted that imbalances between pro-inflammatory cytokines, such as TNF-α, IFN-γ, IL-1β and IL-6, and anti-inflammatory cytokines, including IL-10, IL-4, IL-5 are involved in regulated the inflammatory status. In the present invention, it is found that DSS treatment caused a prominent increase of TNF-α, IFN-γ, and IL-6 in the colon tissues of mice. Interestingly, Pd-Ib greatly reduced the production of TNF-α, IFN-γ, and IL-6 compared with the DSS treatment group, whereas significant effect on the production of IL-4 in a dose-dependent manner is observed (FIG. 13). The results indicated that Pd-Ib could alleviate the DSS-induced inflammation partially contributed to the observed reduction of the pro-inflammatory cytokines TNF-α, IFN-γ, and IL-6 and increasing of IL-4 secreted in colon of DSS-treated mice.

In summary, the present invention indicates that Pd-Ib is effective in alleviating the symptoms of DSS-induced chronic colitis, proving that Pd-Ib is an effective agent in treatment against ulcerative colitis.

INDUSTRIAL APPLICATION

The present invention is in the field of pharmaceuticals and chemical industries. In particular, the present invention relates to a compound, namely (+)-3'-Angeloyloxy-4'-keto-3,4'-dihydroseselin (Pd-Ib), which is isolated from *Bupleurum malconense*. The present invention also includes the methods of preparation and use thereof for treating inflammation, such as in alleviating the symptoms of DSS-induced chronic colitis and as an effective treatment against ulcerative colitis.

What is claimed is:

1. A method of treating or alleviating inflammatory diseases or inflammation comprising administering an effective amount of a compound of structure (I),

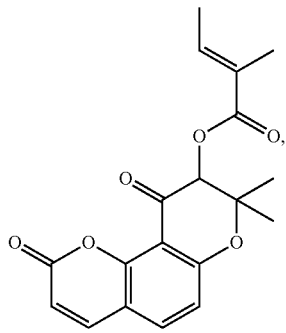

(I)

to a subject in need thereof.

2. The method of claim 1, wherein said inflammatory diseases or inflammation comprises ulcerative colitis, Crohn's disease, and rheumatoid arthritis and said subject is human.

3. The method of claim 1, wherein said effective amount of the compound being administered ranges from 2.43 to 9.72 mg/kg/day of the subject's body weight and said subject is human.

4. The method of claim 1, wherein said effective amount of the compound being administered is 9.72 mg/kg/day of the subject's body weight and said subject is human.

5. The method of claim 3, wherein said effective amount of the compound is administered daily via oral route and for at least seven consecutive days; said subject is human.

6. The method of claim 4, wherein said effective amount of the compound is administered daily via oral route and for at least seven consecutive days; and said subject is human.

* * * * *